United States Patent
Wang et al.

(10) Patent No.: US 7,108,826 B2
(45) Date of Patent: Sep. 19, 2006

(54) HIGH COMPLIANCE, HIGH STRENGTH CATHETER BALLOONS USEFUL FOR TREATMENT OF GASTROINTESTINAL LESIONS

(75) Inventors: Lixiao Wang, Maple Grove, MN (US); Donald J. Fournier, Bellevue, WA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 51 days.

(21) Appl. No.: 11/009,355

(22) Filed: Dec. 10, 2004
(Under 37 CFR 1.47)

(65) Prior Publication Data

US 2005/0119683 A1 Jun. 2, 2005

Related U.S. Application Data (63) Continuation of application No. 08/685,338, filed on Jul. 23, 1996, now abandoned, which is a continuation-in-part of application No. 08/397,837, filed on Mar. 2, 1995, now Pat. No. 5,556,383, which is a continuation-in-part of application No. 08/204,554, filed on Mar. 2, 1994, now abandoned.

(51) Int. Cl.
*B29D 23/00* (2006.01)

(52) U.S. Cl. .................. 264/573; 264/903; 264/905; 264/906

(58) Field of Classification Search ............... 264/573, 264/903, 905, 906
See application file for complete search history.

(56) References Cited

U.S. PATENT DOCUMENTS

| | | | |
|---|---|---|---|
| 4,154,244 A | 5/1979 | Becker et al. | .......... 128/349 B |
| 4,254,774 A | 3/1981 | Boretos | |
| 4,331,786 A | 5/1982 | Foy et al. | |
| 4,332,920 A | 6/1982 | Foy et al. | |
| 4,385,635 A | 5/1983 | Ruiz | |
| 4,413,989 A | 11/1983 | Schjeldahl et al. | ........... 604/96 |
| 4,490,421 A | 12/1984 | Levy | ........................... 428/35 |
| 4,563,181 A | 1/1986 | Wijaymathna | |

(Continued)

FOREIGN PATENT DOCUMENTS

EP 274 411 7/1988

(Continued)

OTHER PUBLICATIONS

U.S. Appl. No. 08/685,338, filed Jul. 23, 1996, Wang et al.

(Continued)

*Primary Examiner*—Suzanne E. McDowell
(74) *Attorney, Agent, or Firm*—Vidas, Arrett & Steinkraus (57) ABSTRACT

Balloon especially useful for dilatation of gastrointestinal lesions have a burst pressure of at least 9 atmospheres, a diameter at 3 atmospheres of about 5 mm or more, and an average compliance over the range of from 3 atmospheres to burst of at least 3% per atmosphere. Such balloons and balloons having other combinations of burst strength, compliance and diameter may be prepared by a method wherein a tubing of a thermoplastic polymer material is radially expanded under a first elevated pressure at an elevated temperature to form the balloon at a first diameter and then annealing the balloon at a second elevated temperature and a second pressure less than the first elevated pressure for a time sufficient to shrink the formed balloon to a second diameter less than the first diameter. The thermoplastic polymer material may be a block copolymer material. Catheters bearing balloons prepared by this method have low withdrawal force requirements, especially catheters used in through-the-scope applications.

13 Claims, 4 Drawing Sheets

U.S. PATENT DOCUMENTS

| | | | |
|---|---|---|---|
| 4,675,361 A | 6/1987 | Ward, Jr. | 525/92 |
| 4,786,556 A | 11/1988 | Hu et al. | 428/412 |
| 4,886,506 A | 12/1989 | Lovgren et al. | |
| 4,898,591 A | 2/1990 | Jang et al. | |
| 4,906,244 A | 3/1990 | Pinchuck et al. | |
| 4,917,667 A | 4/1990 | Jackson | |
| 4,938,676 A | 7/1990 | Jackoski et al. | 425/140 |
| 4,950,239 A | 8/1990 | Gahara et al. | 604/96 |
| 4,950,257 A | 8/1990 | Hibbs et al. | |
| 4,952,357 A | 8/1990 | Enteneuer | 264/129 |
| 5,167,239 A | 12/1992 | Cohen et al. | 128/772 |
| 5,195,969 A | 3/1993 | Wang et al. | 604/96 |
| 5,250,069 A | 10/1993 | Nobuyoshi et al. | |
| 5,264,260 A | 11/1993 | Saab | |
| 5,270,086 A | 12/1993 | Hamlin | 428/35 |
| 5,281,677 A | 1/1994 | Onwunaka et al. | 525/458 |
| 5,290,306 A | 3/1994 | Trotta et al. | |
| 5,295,978 A | 3/1994 | Fan et al. | 604/265 |
| 5,300,048 A | 4/1994 | Drewes, Jr. et al. | 604/280 |
| 5,304,134 A | 4/1994 | Kraus et al. | 604/96 |
| 5,304,340 A | 4/1994 | Downey | |
| 5,328,468 A | 7/1994 | Kaneko et al. | 604/96 |
| 5,335,675 A | 8/1994 | Wheeler et al. | 128/842 |
| 5,344,400 A | 9/1994 | Kaneko et al. | 604/96 |
| 5,348,538 A | 9/1994 | Wang et al. | 604/96 |
| 5,358,486 A | 10/1994 | Saab | |
| 5,397,306 A | 3/1995 | Nobuyoshi et al. | 604/96 |
| 5,478,320 A | 12/1995 | Trotta | 604/96 |
| 5,500,180 A | 3/1996 | Anderson et al. | 264/532 |
| 5,512,051 A | 4/1996 | Wang et al. | 604/96 |
| 5,556,383 A | 9/1996 | Wang et al. | 604/96 |
| 5,714,110 A * | 2/1998 | Wang et al. | 264/529 |
| 5,749,851 A | 5/1998 | Wang | 604/96.01 |
| 5,797,877 A * | 8/1998 | Hamilton et al. | 604/96.01 |
| 5,980,532 A | 11/1999 | Wang | 623/1.11 |
| 6,290,485 B1 | 9/2001 | Wang | 425/470 |
| 6,402,778 B1 | 6/2002 | Wang | 623/1.111 |
| 2002/0183780 A1 | 12/2002 | Wang | 606/194 |

FOREIGN PATENT DOCUMENTS

| | | |
|---|---|---|
| EP | 0 485 903 | 5/1992 |
| EP | 0 513 459 A1 | 11/1992 |
| EP | 420 488 B | 7/1993 |
| EP | 0 566 755 A1 | 10/1993 |
| EP | 566 755 A | 10/1993 |
| EP | 540 858 A | 12/1993 |
| EP | 592 885 A | 4/1994 |
| FR | 2 651 681 | 3/1991 |
| WO | 84/01513 | 4/1984 |
| WO | 92/8512 | 5/1992 |
| WO | 92/19316 | 11/1992 |
| WO | 95/23619 | 9/1995 |
| WO | WO 95/23619 | 9/1995 |
| WO | 96/04951 | 2/1996 |
| WO | WO 96/12516 | 5/1996 |

OTHER PUBLICATIONS

DuPont, "Hytrel©" 11 pg. undated product brochure (received Sep. 1990).

Flesher, "Polyether block amide. high-performance TPE," Modern Plastics, Sep. 1987, pp. 100,105, 110.

Koch, "PEBAX (Polyether Block Amide)", Advances in Polymer Technology, vol. 2, No. 3, 1982 pp. 160-162.

De, et al, eds. *Thermoplastic Elastomer from Rubber-Plastic Blends, Chapter 1*, Ellis Horwoal, New York pp. 13-27.

Gorski, "The Nomenclature of Thermoplastic Elastomers," Kunstoffe German Plastics, 83 (1993) No. 3, pp. 29-30.

Hofmann, "Thermoplastic Elastomers," Kunstoffe German Plastics, 80 (1990) No. 10, pp. 88-90.

Atochem, "Pebax© Resins 33 Series Property Comparison" undated, (1 pg. manufacturers technical information sheet received Sep. 29, 1994).

Atochem, undated and untitled brochure for Pebax³ resins, pp. 2-5.

Bhowmick, et al eds., *Handbook of Elastomers*, Chapters 10 and 12, Marcel Dekker Inc., pp. 341-373 and 411-442.

Walker, et al, eds. *Handbook of Thermoplastic Elastomers*, Chapter 8, Van Nostrand Reinhold Co., NY pp. 258-281.

\* cited by examiner

HIGH COMPLIANCE, HIGH STRENGTH CATHETER BALLOONS USEFUL FOR TREATMENT OF GASTROINTESTINAL LESIONS

CROSS REFERENCE TO RELATED APPLICATION

This application is a continuation of U.S. application Ser. No. 08/685,338, filed Jul. 23, 1996, now abandoned, which is a continuation-in-part of U.S. application Ser. No. 08/397, 837, filed Mar. 2, 1995, now U.S. Pat. No. 5,556,383, which is a continuation-in-part of U.S. application Ser. No. 08/204, 554, filed Mar. 2, 1994, now abandoned.

BACKGROUND OF THE INVENTION

Balloons mounted on the distal ends of catheters are widely used in medical treatment. The balloon may be used to widen a vessel into which the catheter is inserted or to force open a blocked vessel. The requirements for strength and size of the balloons vary widely depending on the balloon's intended use and the vessel size into which the catheter is inserted.

Perhaps the most demanding applications for such balloons are in balloon angioplasty in which catheters are inserted for long distances into extremely small vessels and used to open stenoses of blood vessels by balloon inflation. These applications require extremely thin walled, high strength, relatively inelastic balloons of predictable inflation properties. Thin walls are necessary because the balloon's wall and waist thicknesses limit the minimum diameter of the distal end of the catheter and therefore determine the limits on vessel size treatable by the method and the ease of passage of the catheter through the vascular system. High strength is necessary because when the balloon is used to push open a stenosis, the thin wall must not burst under the high internal pressures necessary to accomplish this task. The balloon must have some elasticity so that the inflated diameter can be controlled, enabling the surgeon to vary the balloon's diameter as required to treat individual lesions, but that elasticity must be relatively low so that the diameter is easily controllable. Small variations in pressure must not cause wide variation in diameter. Such angioplasty balloons have nominal diameters in the range of from about 1.25–4.5 mm.

Outside the field of angioplasty, however, relatively high compliant, high strength materials are desirable for some balloons used on esophageal, pyloric, colonic and anastomotic catheters and scopes.

Major advances in the ability to access remote areas within the gastrointestinal tract have allowed endoscopists to reach obstructive lesions previously accessible only via open surgical techniques. There are three primary approaches available to the clinician for endoscopic treatment of gastrointestinal strictures: 1) Mercury bougie dilatation; 2) Over-the-wire passage of tapered dilators; and 3) Balloon dilation.

Of the three, balloon dilatation is the most recently developed modality. Clinical research studies have been conducted to compare the efficacy of the technique to earlier approaches. For example, in one study evaluating Savary-Guillard® Dilators versus balloon dilators for dilatation of benign esophageal strictures, both methods achieved effective dilatation. However, during the 24 month follow-up, 88% of patients treated with Savary dilators required redilations vs 54% of patients in the balloon group. As a result, the researchers concluded that, over the long term, the balloon may provide superior efficacy. Additional studies have clearly documented the convenience, effectiveness and safety of balloon dilatation of strictures.

An important advantage of balloon dilatation over the alternative techniques is that it enables the clinician to dilate remote strictures throughout the GI tract.

An example is the treatment of esophagal achalasia. The esophagus, a hollow, muscular organ that originates at the pharynx and terminates at the stomach, functions to transport food and fluids from the pharynx to the stomach via a complex, neuromuscular response to the act of swallowing. Specifically, the passage of food or fluid from the pharynx into the esophagus stimulates the peristaltic contractions designed to propel the contents forward through the esophagus. Concurrently, the lower esophageal sphincter (LES) at the gastroesophagal junction relaxes allowing the passage of esophageal contents into the stomach. Reflux of stomach contents back into the esophagus is prevented by closure of the LES. Achalasia is a disorder of unknown etiology that disrupts the normal esophageal function (3,4). In this disorder, two deficits are present. First, the normal esophagal peristaltic wave is absent. Second, the lower esophageal sphincter does not relax. The result is esophageal dilatation and severe, progressive dysphagia. Treatment for achalasia is aimed at reduction of LES pressure. This is accomplished nonsurgically via forceful balloon dilatation of the sphincter.

Biliary dilatation may also be performed by such balloon catheter dilatation. Biliary strictures may result from variety of processes including postoperative scarring, inflammation, or malignancy. Endoscopic balloon dilatation of these lesions has been shown to be an effective treatment approach.

There therefore is a need for effective devices which permit endoscopic dilatation of lesions throughout the alimentary tract. It is important that the catheters offer first-use effectiveness in an advanced design to permit rapid inflation, deflation and easy scope passage. The balloons for such devices desirably would have a long dilation length, high operating pressure, typically greater than 50 psi (3 atm, 344.7 kPa) and desirably up to 146 psi, (10 atm, 1013 kPa), low withdrawal force and high compliance. For instance, a compliance change is desirable which would allow a balloon having a 1.25–3.0 mm nominal diameter at 3 atm to grow in a generally linear manner at least 0.25 mm, preferably about 0.5 mm, or more as pressure is increased from 3 to 12 atm. For balloons about 3.25–6.0 mm nominal diameter, a growth of at least 1.0 mm over the same range would be desirable. For balloons in the range of about 6–12 mm nominal diameter, a growth of at least 2.0 mm over a 3–10 atm pressure range would be desirable. For even larger diameter balloons, for instance balloons having 3 atm diameters of 12–30 mm, a compliance curve which provides growth of about 3 mm or more, preferably about 4.0 mm or more, over the range of 3 to 9 atm is desirable.

In U.S. Pat. No. 5,348,538, incorporated herein by reference, there is described a single layer angioplasty balloon made of a material such as PET which follows a stepped compliance curve. The stepped compliance curves of these balloons have a low pressure segment following a first generally linear profile, a transition region, typically in the 8–14 atm range, during which the balloon rapidly expands yielding inelastically, and a higher pressure region in which the balloon expands along a generally linear, low compliance curve. The stepped compliance curve allows a physician to dilate different sized lesions without using multiple balloon catheters.

A polyethylene ionomer balloon with a stepped compliance curve is disclosed in EP 540 858.

In copending U.S. application Ser. No. 08/392,837, filed 2 Mar. 1995, entitled Block Copolymer Elastomer Catheter Balloons, incorporated herein by reference, which corresponds to WO 95/23619, there are described balloons, useful on angioplasty catheters and similar medical devices, which are made from certain block copolymer materials which provide an unusual combination of compliance, softness and strength properties.

Block copolymer balloons for balloon catheters, prepared using a particular heat set technique to stabilize the balloon dimensions, are also described in U.S. Pat. No. 5,500,180.

SUMMARY OF THE INVENTION

The invention provides balloons having the desired properties just described. In one aspect, the invention is a method for forming a balloon for a medical device in which a tubing of a thermoplastic polymer material is radially expanded under a first elevated pressure at a first elevated temperature to form the balloon at a first diameter, the thermoplastic polymer material being a block copolymer material and the method including the further step of annealing the balloon at a second elevated temperature less than or equal to the first temperature and a second pressure less than the first elevated pressure for a time sufficient to shrink the formed balloon to a second diameter less than the first diameter. Suitably the second temperature is in the range of 70–100° C., the second pressure is no more than about 50 psi, and the time of annealing is sufficient to shrink the balloon so that its diameter at 3 atm pressure is about 90% or less, preferably about 85% or less, of the 3 atm diameter of a correspondingly prepared balloon prepared without said shrinking step.

In some embodiments to improve balloon-to-balloon reproducibility of the process, the balloon may be shrunk at a very low inflation pressure (typically 0–10 psi) to a nominal diameter below that desired in the final balloon, and then pressurized at a pressure between the shrink pressure and 50 psi, at a temperature within the same range within a mold or cylinder which is sized to provide the desired nominal diameter, still below the diameter at which the balloon was initially blown, and suitably 90% or less of the initial blow diameter.

The shrinking process used in the invention is quite different from the heat set technique used in U.S. Pat. No. 5,500,180, in that the process of U.S. Pat. No. 5,500,180, after formation of the balloon heats the balloon under pressure of 100–500 psi to a temperature above the blowing temperature specifically for the purpose of stabilizing the balloon against shrinkage upon cooling. The present invention is directed to exploitation of shrinkage behavior in order to increase the compliance of the resulting balloon.

Balloons made of multiple layers of thermoplastic material, such as coextruded balloons of the types described in U.S. Pat. Nos. 5,195,969, 5,270,086, and 5,478,320, or separately blown dual layer balloons of the types described in U.S. Pat. No. 5,512,051, WO 96/04951 and in copending application Ser. No. 08/611,644, filed 6 Mar. 1996, all incorporated herein by reference, may also be employed in the present invention by shrinking the so-formed balloon in accordance with the present invention after it has been formed.

As further aspects of the invention, there are described herein balloons particularly suited to dilation of GI lesions of various types which are characterized by unique combinations of balloon diameter, high burst strength and high compliance characteristics.

The high strength, high compliance balloons of the invention also provide excellent rewrap characteristics, in comparison to high strength balloons formed by other processes. Consequently, after treatment of a lesion and deflation of the balloon, the force required to withdraw the balloon catheter from the body is low, especially for catheters designed to pass through endoscopes (TTS).

DETAILED DESCRIPTION OF THE INVENTION

Typically, balloon dilatation catheters for gastrointestinal applications are available in two design options: 1) through-the scope (TTS); and 2) over-the-wire (OTW). Each design offers particular advantages in specific clinical situations.

Figure 1:
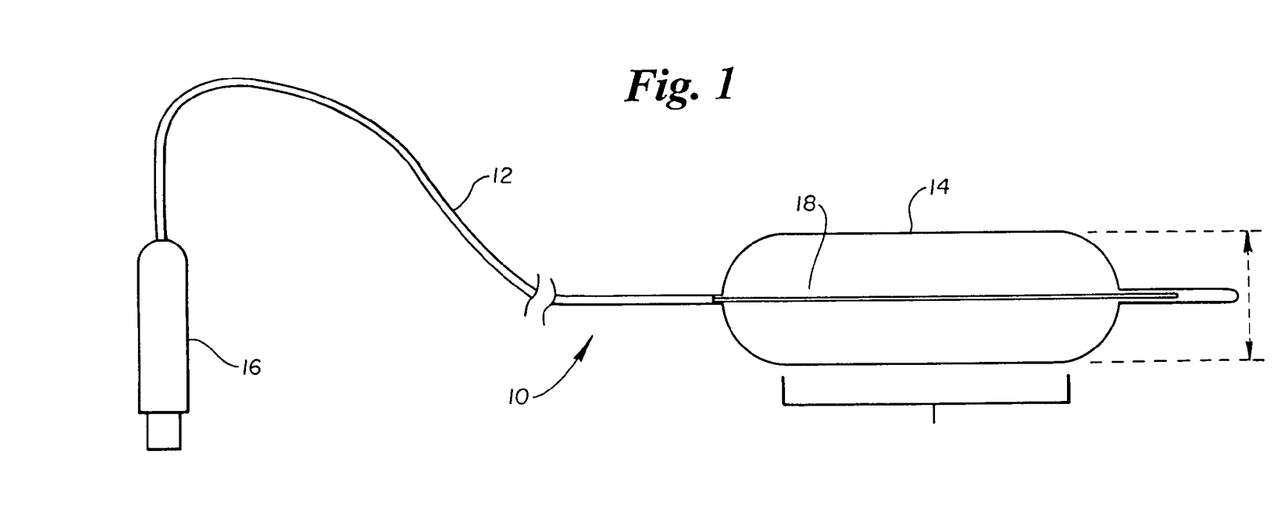
FIG. 1 is a schematic side view of a through-the scope dilatation catheter of the invention.

Referring to FIG. 1, a TTS balloon dilatation catheter 10 is shown. Catheter 10 comprises a shaft 12, a balloon 14 near the distal end thereof and an inflation apparatus 16 at the proximal end thereof. Shaft 12 has a strong flexible kink-resistant construction and includes a longitudinal lumen extending therethrough by means of which the balloon 14 may be inflated by the inflation apparatus 16. Catheter 10 is designed for direct passage through the working channel of the endoscope to the site of an obstructive lesion. Because TTS catheters are not passed over a guidewire, the design includes a mechanism for stiffening the shaft enough to allow advancement through the narrow scope channel to the lesion. To achieve this result, TTS catheters suitably incorporate a stiffening stylet 18 within the shaft. This stylet extends from the proximal end of the shaft through the length of the balloon and provides the stiffness required to facilitate passage through an endoscope and enhance appropriate positioning within the lesion.

TTS balloon dilatation catheters are useful when an endoscopist prefers to dilate under direct visualization. With the endoscope placed immediately proximal to the lesion, catheter advancement and balloon inflation can be directly monitored. Scope placement immediately proximal to the balloon also assists in maintaining proper balloon position during inflation. For example, during dilatation of pyloric structures, the balloon has a tendency to slip proximally or distally during inflation. By positioning the scope at the proximal end of the balloon, the endoscopist is able to mechanically block any backward movement during inflation thereby facilitating efficient, effective dilatation.

Figure 2:
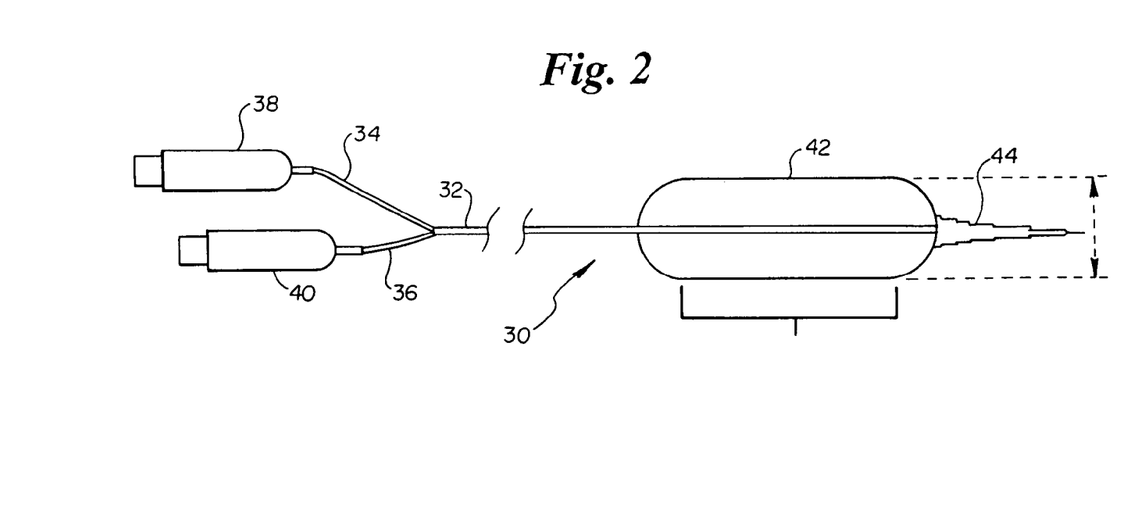
FIG. 2 is a schematic side view of a dual lumen over-the wire dilatation catheter of the invention.

FIG. 2 illustrates the construction of an OTW balloon dilation catheter 30. Catheter 30 includes a shaft 32 which has a strong flexible kink-resistant construction and incorporates a double-lumen design. This design provides a lumen for guidewire passage and a lumen for balloon inflation. At the proximal end of catheter 30 the lumens of shaft 32 divide into separate portions 34, 36 which communicate respectively to balloon inflation apparatus 38 and to guidewire control apparatus 40. A balloon 42 is mounted on the shaft 32 near the distal end of catheter 30. Catheter 30 may incorporate a soft flexible tip 44 to provide less traumatic advancement through tortuous or narrow strictures. Tip 44 may be radiopaque to assist in fluoroscopic positioning of the catheter at the lesion site.

OTW balloon dilatation catheters are the preferred design option when extremely tortuous of difficult anatomy is encountered. In these cases, the ability to track the catheter over a previously placed guidewire enhances the clinician's ability to precisely position the balloon for effective dilatation. Further, for colonic lesions distal to scope access, a fluoroscopically-guided, OTW placement technique can be used to achieve appropriate positioning.

With OTW balloon dilatation catheters, the endoscopist typically monitors balloon inflation fluoroscopically rather than under direct visualization. Therefore, these dilators incorporate radiopaque markers to aid in accurate positioning. These catheters are designed to be used with guidewires and are available in a variety of shaft and balloon lengths and diameters. This allows the endoscopist to select a catheter appropriate for each lesion.

With regard to balloon size selection, for successful dilatation, the balloon must provide effective radial force against the entire length of the stricture. In FIGS. 1 and 2 the balloon diameter is indicated by dimension A and the dilation length indicated by dimension B. The balloon should be long enough to dilate the entire length of the stricture. The inflated outer diameter should affect the desired degree of dilatation.

The length of the catheter shaft required varies with the location of the stricture. For example, catheters 180 cm in length allow access to esophageal and pyloric lesions, while a catheter 240 cm in length is required for colonic strictures.

With the exception of Achalasia Balloon Dilators which are inflated with air, balloons are primarily inflated with water, saline or a contract/saline mixture. The latter is used with OTW balloon catheters to enhance visualization. It is important not to exceed the maximum inflation pressure specified for any particular balloon catheter. Surpassing this pressure could lead to balloon rupture.

During a procedure the balloon is fully inflated to the desired dilatation diameter. Dilatation force is applied for as long as necessary to achieve desired results. Using an inflation apparatus equipped with a pressure gauge, the balloons of the present invention provide a substantially wider range of stricture diameters which may be treated with a single catheter. After treatment, the deflated balloons of the invention provide substantially reduced resistance to withdrawal of the catheter from the body compared to prior art high strength balloons made for instance from biaxially oriented PET. In some TTS applications measured withdrawal force through the scope for catheters bearing balloons of the invention has been found to be only about ½ of the withdrawal force for corresponding catheters bearing PET balloons of similar burst strength.

For esophageal balloon dilatation TTS catheters, a balloon of approximately 8 cm length (dimension B), having an outer diameter (dimension A) of 6 to 20 mm is suitable. The preferred length of the catheter is 180 cm.

For pyloric balloon dilatation TTS catheters, a balloon of approximately 5.5 cm length balloon, having an outer diameter of 6 to 20 mm is suitable. The preferred length of the catheter is 180 cm.

For colonic balloon dilatation TTS catheters, a balloon of approximately 5.5 cm length balloon, having an outer diameter of 6 to 20 mm is suitable. The preferred length of the catheter is 240 cm.

For anastomotic balloon dilatation TTS catheters, a balloon of approximately 8 cm length balloon, having an outer diameter of 20–30 mm is suitable. The preferred length of the catheter is 240 cm.

Preferred balloon materials are block copolymers or blends of flexible and rigid thermoplastic polymers. Particularly preferred are thermoplastic block copolymers characterized as follows:

the block copolymer is made up of hard segments of a polyester or polyamide and soft segments of polyether;
the polyester hard segments are polyesters of an aromatic dicarboxylic acid and a $C_2$–$C_4$ diol,
the polyamide hard segments are polyamides of $C_6$ or higher, preferably $C_{10}$–$C_{12}$, carboxylic acids and $C_6$ or higher, preferably $C_{10}$–$C_{12}$, organic diamines or of $C_6$ or higher, preferably $C_{10}$–$C_{12}$, aliphatic ω-amino-α-acids, and
the polyether soft segments are polyethers of $C_2$–$C_{10}$, preferably $C_4$–$C_6$ diols; and
the percentage by weight of the block polymer attributable to the hard segments is between about 50% and about 98%. Suitably the block copolymer has a low flexural modulus, namely less than 150,000 psi, preferably less than 120,000 psi, and has a hardness, Shore D scale, of greater than 60. From such polymers, balloons having very high compliance profiles can be prepared with high wall strength. The low flexural modulus contributes to a softer feel found with the balloons of the invention, compared to those made of other high strength polymer material.

The preferred balloons of the invention are made of polyamide/polyether block copolymers. The polyamide/polyether block copolymers are commonly identified by the acronym PEBA (polyether block amide). The polyamide and polyether segments of these block copolymers may be linked through amide linkages, however, most preferred are ester linked segmented polymers, i.e. polyamide/polyether polyesters. Such polyamide/polyether/polyester block copolymers are made by a molten state polycondensation reaction of a dicarboxylic polyamide and a polyether diol. The result is a short chain polyester made up of blocks of polyamide and polyether. The polyamide and polyether blocks are not miscible. Thus the materials are characterized by a two phase structure: one is a thermoplastic region that is primarily polyamide and the other is elastomer region that is rich in polyether. The polyamide segments are semicrystalline at room temperature. The generalized chemical formula for these polyester polymers may be represented by the following formula:

in which PA is a polyamide segment, PE is a polyether segment and the repeating number n is between 5 and 10.

The polyamide segments are suitably aliphatic polyamides, such as nylons 12, 11, 9, 6, 6/12, 6/11, 6/9, or 6/6. Most preferably they are nylon 12 segments. The polyamide segments may also be based on aromatic polyamides but in such case significantly lower compliance characteristics are to be expected. The polyamide segments are relatively low molecular weight, generally within the range of 500–8,000, more preferably 2,000–6,000, most preferably about 3,000–5,000.

The polyether segments are aliphatic polyethers having at least 2 and no more than 10 linear saturated aliphatic carbon atoms between ether linkages. More preferably the ether segments have 4–6 carbons between ether linkages, and most preferably they are poly(tetramethylene ether) segments. Examples of other polyethers which may be employed in place of the preferred tetramethylene ether segments include polyethylene glycol, polypropylene glycol, poly(pentamethylene ether) and poly(hexamethylene ether). The hydrocarbon portions of the polyether may be optionally branched. An example is the polyether of 2-ethylhexane diol. Generally such branches will contain no more than two carbon atoms. The molecular weight of the polyether segments is suitably between about 400 and 2,500, preferably between 650 and 1000.

The weight ratio of polyamide to polyether in the polyamide/polyether polyesters used in the invention desirably should be in the range of 50/50 to 98/2, preferably between 60/30 and 92/08, more preferably, between 70/30 and 90/10.

Polyamide/polyether polyesters are sold commercially under the Pebax® trademark by Atochem North America, Inc., Philadelphia Pa. Examples of suitable commercially available polymers are the Pebax® 33 series polymers with hardness 60 and above, Shore D scale, especially Pebax® 7233, 7033 and 6333. These polymers are made up of nylon 12 segments and poly(tetramethylene ether) segments in different weight ratios and segment lengths.

It is also possible to use other PEBA polymers with the physical properties specified herein and obtain similar compliance, strength and softness characteristics in the finished balloon.

As an alternative to polyamide elastomers, it is also possible to utilize polyester/polyether segmented block copolymers and obtain similar balloon properties. Such polymers are made up of at least two polyester and at least two polyether segments. The polyether segments are the same as previously described for the polyamide/polyether block copolymers useful in the invention. The polyester segments are polyesters of an aromatic dicarboxylic acid and a two to four carbon diol.

Suitable dicarboxylic acids used to prepare the polyester segments of the polyester/polyether block copolymers are ortho-, meta- or para-phthalic acid, napthalenedicarboxylic acid or meta-terphenyl-4,4'-dicarboxylic acids.

Preferred polyester/polyether block copolymers are poly (butylene terephthalate)-block-poly(tetramethylene oxide) polymers such as Arnitel EM 740, sold by DSM Engineering Plastics. Hytrel polymers, sold by DuPont which meet the physical and chemical specifications set out herein can also be used.

It is preferred that the block copolymers have a hardness, Shore D scale, of at least 60 and a flexural modulus of no more than about 150,000, in order to obtain optimal strength, compliance and softness characteristics. Preferably the Shore D hardness is in the range of 65–75 and the flexural modulus is in the range of 50,000–120,000. The preferred polymers useful in the invention are also characterized by a high ultimate elongation of about 300% or higher and an ultimate tensile strength of at least 6,000 psi.

Other thermoplastic polymer materials which may be used to prepare balloons in accordance with the invention include blends of rigid and flexible polymers; polyurethanes which have flexible portions, typically derived from polyester or polyether polyols and rigid portions, typically derived from diisocyanates; random copolymers of rigid and flexible monomers; aliphatic polyketones; polysulfides such as PPS (polyphenylenesulfide); polyamides, for instance $C_6$ or higher polyamides which are saturated with water, $C_{11}$ or higher polyamide homopolymers regardless of water content, and polyamide copolymers of linear and branched monomer units; and other polymers or polymer blends which are known in the art as thermoplastic elastomers. Specific additional thermoplastic polymer products which are considered suitable include polyurethane/polycarbonate blend or block copolymers sold under the trademarks, TEXIN TPU by Bayer Corp and TECOTHANE by Thermedics Inc. and polyurethanes sold under the trademark PELLETHANE by Dow Chemical Co. As previously mentioned, multilayer balloon structures formed by concentric coextrusion of different thermoplastic polymers, or by sequential concentric blowing of separate tubing parisons of different materials, may also be employed.

Manufacture of balloons of the invention is started with an extruded tubing of the thermoplastic polymer material.

The balloon, prior to its being shrunk, may be manufactured in accordance with known techniques such as described in copending application Ser. No. 08/392,837, filed 2 Mar. 1995, entitled Block Copolymer Elastomer Catheter Balloons, incorporated herein by reference, which corresponds to WO 95/23619, and Ser. No. 08/555,219, filed 8 Nov. 1995, entitled Method of Balloon Formation by Cold Drawing/Necking, incorporated herein by reference. Multistaged blowing techniques as described in copending application Ser. No. 08/197,639, filed 17 Feb. 1994, also incorporated herein by reference, may also be employed.

The balloon shrinking process is similar to that described in U.S. Pat. No. 5,348,538 for balloons of non-compliant material such as PET. However, the balloons of the invention are desirably constructed by blowing the balloon from a block copolymer or other polymer material as described above and then shrinking the balloon to a greater extent than was done in the specific illustrative examples of U.S. Pat. No. 5,348,538. The amount of shrinkage is controlled by the pressure maintained in the balloon during annealing and the temperature and time of the annealing. For a balloon made from Pebax® 7233, the blowing pressure is suitably in the range 200–400 psi, and temperature is suitably in the range of 90–100° C., and the annealing pressure is in the range of 0–50, preferably 1–30 psi at 70–100° C. for 3–30 seconds.

By shrinking until the balloon, at 3 atm pressure, provides a diameter of about 90% or less, preferably 85% or less, and more preferably about 65%–75% of the diameter of a correspondingly prepared balloon, at 3 atm pressure, which does not undergo shrinking, a very steep compliance curve is obtained which is more generally linear, the greater the shrinkage. Burst strength is not substantially affected by the shrinking step. However the shrinking step causes the compliance curve to start from a lower point so that overall the balloon is much more compliant. In this manner the comparatively high strength of the block copolymer material is made accessible to medical device applications where high compliance is also desirable.

To improve balloon-to-balloon reproducibility of the process, the balloon may be shrunk at a very low inflation pressure (typically 0–30 psi) to a nominal diameter below that desired in the final balloon, and then pressurized at a pressure between the shrink pressure and 50 psi, at a temperature within the same range within a mold or cylinder which is sized to provide the desired nominal diameter, still below the diameter at which the balloon was initially blown, and suitably 90% or less of the initial blow diameter. Example 10 is illustrative of this technique.

The invention is illustrated by the following non-limiting examples.

EXAMPLE 1 (COMPARATIVE EXAMPLE)

Pebax® 7233 tubes with dimensions of 0.105 inch ID (inner diameter)×0.140 OD (outer diameter) are cold-drawn at a very low temperature, approximately in the range of −100° C. to −20° C. as follows. A screw driven stretching machine with a pair of pneumatic grippers is used to stretch the tubing. The center portion of the tube is cooled by directly spraying liquid $N_2$ on the center portion. Five 50 mm length balloons are blown at 95° C. in a 16 mm diameter mold using a blowing pressure of 260 psi and a tension of 160 grams. The average double wall thickness of the balloons was 0.00282 inch. The burst pressure was 9.2 atm. The compliance from 3 atm to 5 atm was 4.2% and from 3 atm to burst pressure was 11.7%.

EXAMPLE 2

Five balloons were prepared as in Example 1. The balloons, while inflated at about 5 psi pressure, were shrunk by dipping in a 80° C. water bath for 5 minutes. The average double wall thickness after shrinking was 0.00429 inch. The average burst pressure of the balloons was 9.4 atm. The compliance from 3 atm to 5 atm was 15% and from 3 atm to burst pressure was 39%.

EXAMPLE 3 (COMPARATIVE EXAMPLE)

Pebax® 7233 tubes with dimensions of 0.0264 inch ID×0.0464 OD (outer diameter) are cold-drawn as in Example 1. A 4 mm balloon is blown at 95° C. in a mold using a blowing pressure of 450 psi and a tension of 300 grams. The burst pressure was 22 atm.

EXAMPLE 4

The process of Example 2 is repeated except that the shrinking step is performed by annealing the balloons while inflated to 2 atm pressure in water baths under different conditions, namely: 75° C. for 10 seconds; 75° C. for 30 seconds; 75° C. for 60 seconds; and 95° C. for 10 seconds. Compliance curves for the balloons of Examples 3 and 4 are plotted in FIG. 3.

EXAMPLE 5

Balloons were prepared as in Examples 1 and 2 using Pebax 7033 polymer and the conditions specified in Table 1. The compliance results are summarized in Table 1 and are plotted in FIG. 4.

EXAMPLE 6

Balloons were made from Arnitel EM 740 polymer tubing by stretching tubing as specified in Table 2 at room temperature at a stretch ratio of 4.2 and then blowing the balloon from the stretched tubing under the conditions specified in Table 2. The compliance results are summarized in Table 2 and are plotted in FIG. 5.

TABLE 1

| Sample | Mold Dia (mm) | Length (mm) | Tube ID × OD (inch) | Blowing pressure (atm) | Blowing tension (g) | Double wall thickness | Shrinking temp. ° C. | Shrinking time\min | Burst pressure (atm) | Compliance 3 atm-burst % | Compliance %/atm |
|---|---|---|---|---|---|---|---|---|---|---|---|
| 5A | 9 | 50 | .0515 × .0545 | 400 | 130 | .00213 | none | none | 15 | 15% | 1.25 |
| 5B | 9 | 50 | .0515 × .0545 | 400 | 130 | .00285 | 80 | 5 | 14 | 49% | 4.45 |
| 5C | 12 | 50 | .098 × 0.132 | 300 | 190 | .00281 | none | none | 11 | 15% | 1.375 |
| 5D | 12 | 50 | .098 × 0.132 | 300 | 190 | .0044 | 81 | 5 | 11 | 47% | 5.875 |
| 5E | 18 | 50 | 0.118 × 0.158 | 350 | 250 | .00295 | none | none | 10 | 11% | 1.83 |
| 5F | 18 | 50 | 0.118 × 0.158 | 350 | 250 | .00457 | 81 | 5 | 9 | 28% | 4.66 |
| 5G | 20 | 80 | 0.135 × 0.175 | 300 | 175 | .00290 | none | none | 9 | 9% | 1.50 |
| 5H | 20 | 80 | 0.135 × 0.175 | 300 | 175 | .00413 | 80 | 1 | 9 | 27% | 4.50 |

TABLE 2

| Mold Diameter (mm) | Length (mm) | Tube ID × OD (inch) | Blowing pressure (atm) | Blowing tension (g) | Double wall thickness | Shrinking temp. ° C. | Shrinking time\min | Burst pressure (atm) | Compliance 3 atm-burst % | Compliance %/atm |
|---|---|---|---|---|---|---|---|---|---|---|
| 5.5 | 50 | .046 × .084 | 350 | none | .00275 | none | none | 16 | 27% | 2.00 |
| 5.5 | 50 | .046 × .084 | 350 | none | .00360 | 80 | 1 | 16 | 70% | 5.38 |

Figure 3:
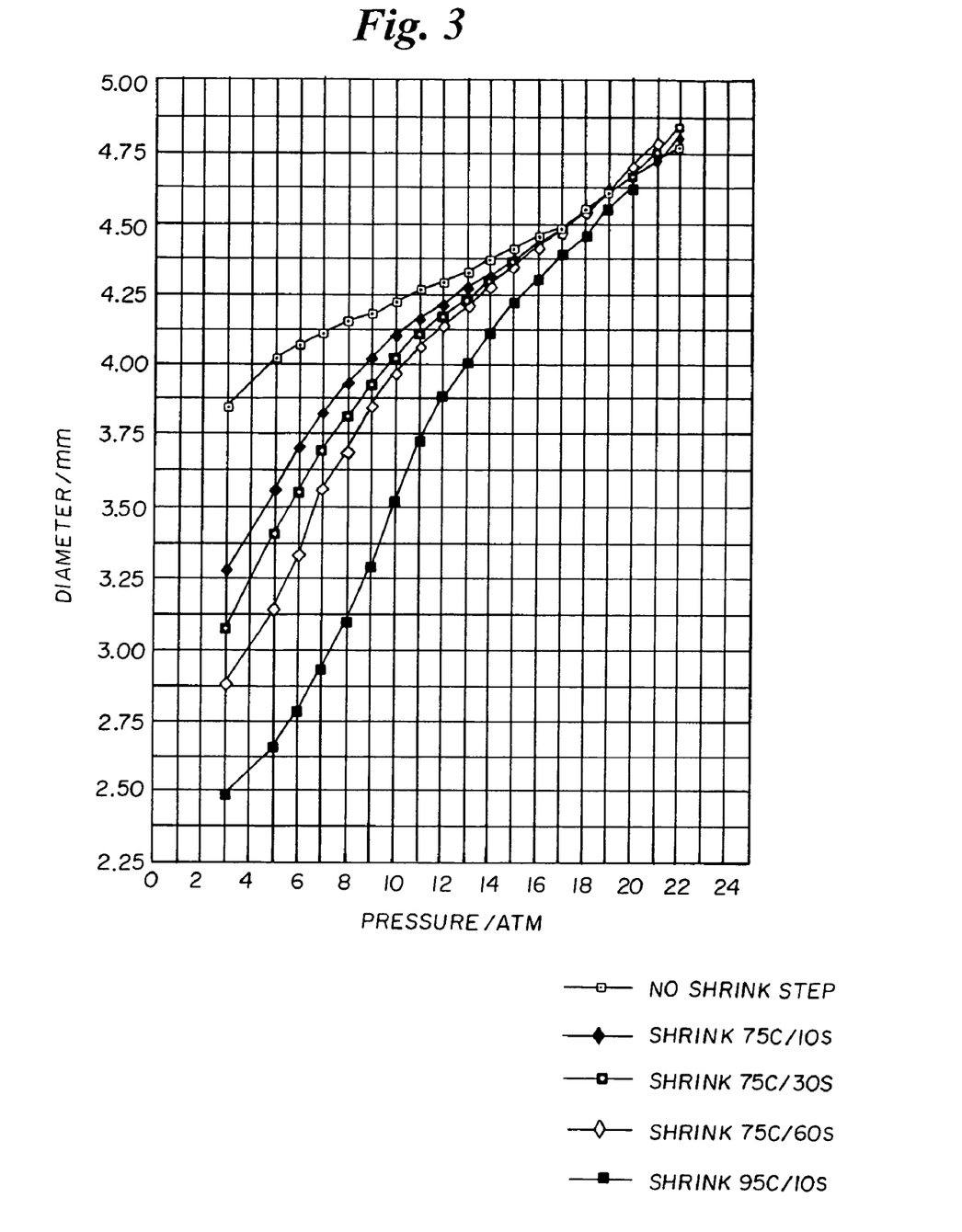
FIG. 3 is a plot showing compliance curves of balloons prepared in Examples 3 and 4.
Figure 4:
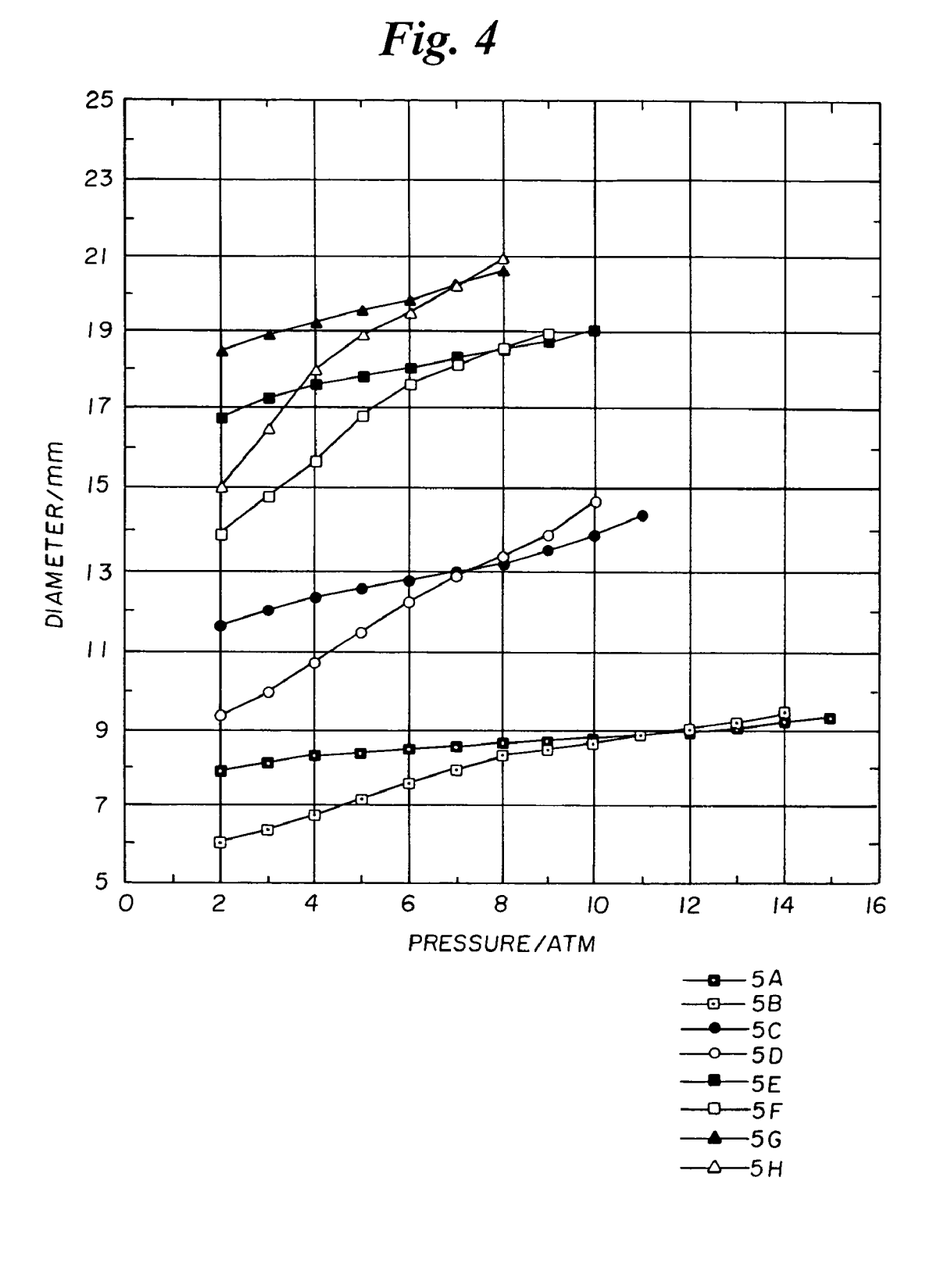
FIG. 4. is a plot showing compliance curves of balloons prepared in Example 5.
Figure 5:
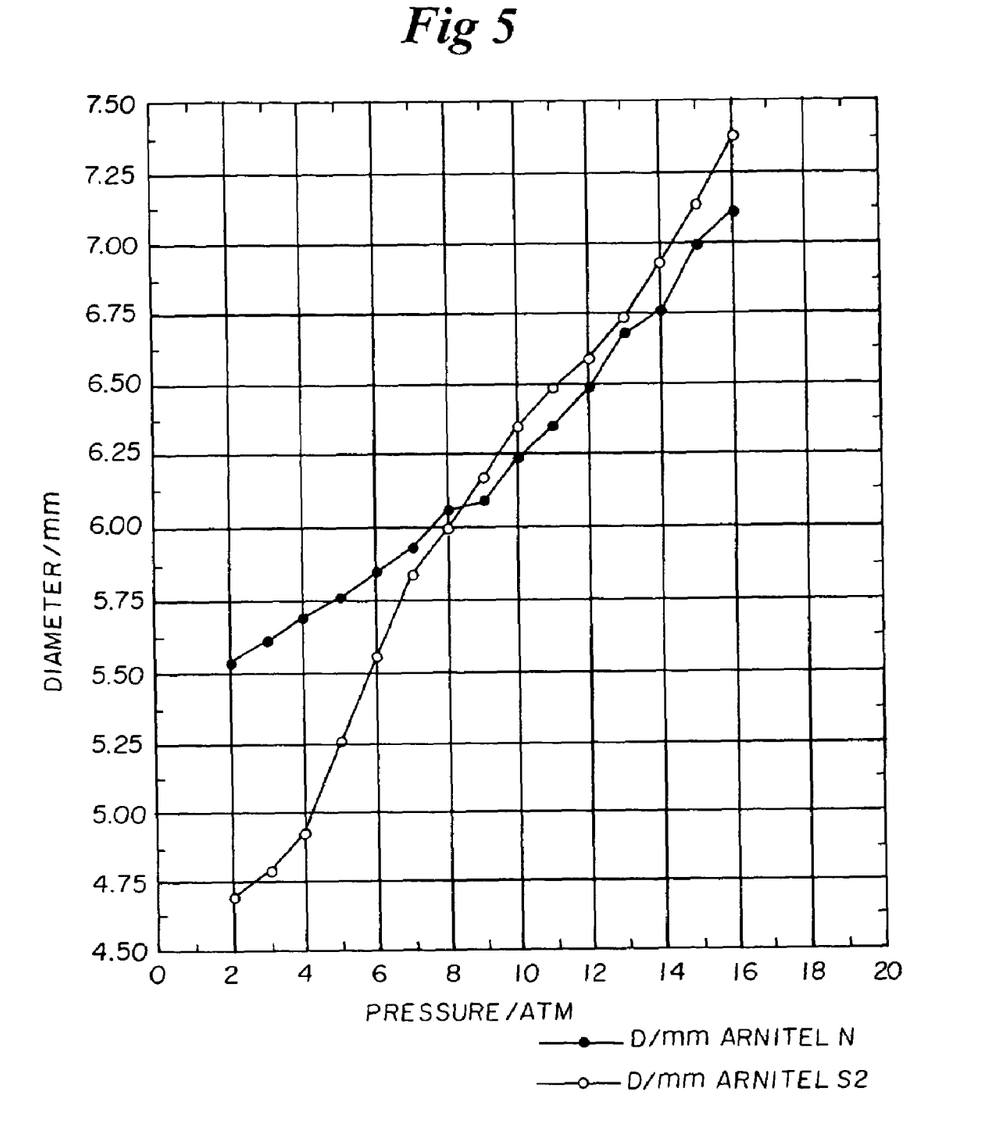
FIG. 5 is a plot showing compliance curves of balloons prepared in Example 6.

As can be seen from FIGS. 3–5, the balloons prepared utilizing the shrinking step have very high compliance profiles, in addition to high wall strength. The shrinking step causes the compliance curve to start from a lower point so that overall the balloon is much more compliant. In this manner the comparatively high strength of the block copolymer material is made accessible to medical device applications where high compliance is also desirable.

EXAMPLE 9 (COMPARATIVE EXAMPLE)

Extruded Pebax 7233 tubes with dimensions of 0.0509 inch ID×0.0729 inch OD were prepared. Five 55 mm length balloons were blown at a temperature of 95° C. in an 8 mm diameter mold using a blowing pressure of 450 psi and a tension of 150 grams. The average double wall thickness of the balloons was 0.00174 inch. The average burst pressure was 13.6 atm. The compliance from 3 atm to 10 atm was 9.0%, and from 3 atm to burst pressure was 15%.

EXAMPLE 10

Five balloons were prepared as in Example 9. The balloons while at a tension and inflated at atmospheric pressure were shrunk by dipping in an 85° C. water bath for 2 minutes. The balloons were then each inserted into a 5.6 mm ID glass tube, replaced in the 85° bath and pressurized at 30 psi for 2 minutes. The resulting balloons had an average double wall thickness of 0.00233 inch, an average burst pressure of 12.6 mm, a compliance from 3 atm to 10 atm of 36% and a compliance from 3 atm to burst of 44%.

The above disclosure is intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A method of forming a balloon for a medical device, wherein a tubing of a thermoplastic polymer material is radially expanded under a first elevated pressure at an elevated temperature to form the balloon at a first diameter, the thermoplastic polymer material being a block copolymer material and the method including the further step of annealing the balloon at a second elevated temperature less than the first elevated temperature and a second pressure less than the first elevated pressure for a time sufficient to shrink the formed balloon to a second diameter less than the first diameter, and wherein said annealing step occurs prior to sterilization of the medical device.

2. A method as in claim 1 wherein the temperature, time and pressure of the annealing step are selected so that the diameter of the balloon at 3 atm pressure is about 90% or less of the 3 atm diameter of a correspondingly prepared balloon prepared without said shrinking step.

3. The method as in claim 1, wherein the block copolymer is made up of soft segments of a polyether and hard segments of a polyester or a polyamide.

4. The method as in claim 3, wherein the second pressure is no more than 20 psi.

5. The method as in claim 4, wherein the first elevated temperature is within the range of 90–100EC and the second elevated temperature is within the range of 70–100EC and is less than the first elevated temperature.

6. The method as in claim 3, wherein the polyether soft segments are polyethers of $C_2$–$C_{10}$ diols.

7. The method as in claim 3, wherein the hard segments are polyesters of an aromatic dicarboxylic acid and a $C_2$–$C_4$ diol.

8. The method as in claim 3, wherein the hard segments are polyamides chosen from the group consisting of the combination of $C_6$ or higher carboxylic acids and $C_6$ or higher organic diamines and $C_6$ or higher, aliphatic $\omega$-amino-$\alpha$-acids.

9. The method as in claim 1, wherein the second pressure is within the range of 1–10 psi.

10. A method of forming a balloon for a medical device comprising:
    radially expanding tubing of thermoplastic polymer material under elevated blowing pressure greater than 50 psi at an elevated blowing temperature to form the balloon to have a first diameter at 3 atm inflation pressure,
    annealing the formed balloon prior to sterilization of the medical device at an elevated annealing temperature less than or equal to the blowing temperature, and at an annealing pressure which in the range of 0–20 psi, for a time sufficient to shrink the formed balloon to have a second diameter at 3 atm inflation pressure which is less than 90% of the first diameter, and then
    pressurizing the balloon in a fixed diameter form, said fixed diameter being greater than said second diameter but no more than 90% of said first diameter, at a pressure above the annealing pressure but no more than 50 psi and a temperature not less than said annealing temperature and not greater than said blowing temperature for a time to provide the balloon with a final diameter at 3 atm inflation pressure which is greater than said second diameter but not more than 90% of said first diameter.

11. A method as in claim 10 wherein said final diameter is 85% or less of said first diameter.

12. A method as in claim 10 wherein said final diameter is 65–75% of said first diameter.

13. A method as in claim 10 wherein the thermoplastic polymer material is a block copolymer, a thermoplastic elastomer, a polymer blend, a random copolymer of rigid and flexible monomers, polyurethanes which have rigid and flexible portions, polyketones, polysulfides or a polyamide homopolymer or copolymer.

* * * * *